(12) United States Patent
Matheny et al.

(10) Patent No.: US 8,709,076 B1
(45) Date of Patent: Apr. 29, 2014

(54) TWO-PIECE PROSTHETIC VALVE

(71) Applicant: Francis Law Group, Alameda, CA (US)

(72) Inventors: Robert Matheny, Norcross, GA (US); Zachary Reinhardt, Alpharetta, GA (US)

(73) Assignee: Cormatrix Cardiovascular, Inc., Roswell, GA (US)

( * ) Notice: Subject to any disclaimer, the term of this patent is extended or adjusted under 35 U.S.C. 154(b) by 0 days.

(21) Appl. No.: 13/782,289

(22) Filed: Mar. 1, 2013

(51) Int. Cl.
*A61F 2/24* (2006.01)

(52) U.S. Cl.
USPC .......................................... 623/2.13; 623/2.1

(58) Field of Classification Search
USPC ............. 623/1.24, 1.26, 1.47, 2.1, 2.12–2.18, 623/2.42

See application file for complete search history.

(56) References Cited

U.S. PATENT DOCUMENTS

| | | | |
|---|---|---|---|
| 7,758,632 B2 * | 7/2010 | Hojeibane et al. | 623/1.24 |
| 2005/0075725 A1 * | 4/2005 | Rowe | 623/2.14 |
| 2006/0195183 A1 * | 8/2006 | Navia et al. | 623/2.18 |
| 2006/0217802 A1 * | 9/2006 | Ruiz et al. | 623/2.11 |

FOREIGN PATENT DOCUMENTS

WO  WO 2012/087606  * 6/2012 ............... A61K 9/00

* cited by examiner

*Primary Examiner* — David Isabella
*Assistant Examiner* — Dinah Baria
(74) *Attorney, Agent, or Firm* — Francis Law Group

(57) ABSTRACT

A two-piece prosthetic valve having first and second members, a first end of the first member being sized and configured to receive a second end of the second member therein, the second end of the second member being attached to the first member at at least one commissure connection point to form at least one leaflet therein.

19 Claims, 3 Drawing Sheets

TWO-PIECE PROSTHETIC VALVE

FIELD OF THE INVENTION

The present invention generally relates to prosthetic valves for replacing defective cardiovascular valves. More particularly, the present invention relates to two-piece prosthetic valves for replacing defective aortic, pulmonary, mitral, tricuspid and/or peripheral venous valves.

BACKGROUND OF THE INVENTION

As is well known in the art, the human heart has four valves that control blood flow circulating through the human body. On the left side of the heart is the mitral valve, located between the left atrium and the left ventricle, and the aortic valve, located between the left ventricle and the aorta. Both of these valves direct oxygenated blood from the lungs into the aorta for distribution through the body.

The tricuspid valve, located between the right atrium and the right ventricle, and the pulmonary valve, located between the right ventricle and the pulmonary artery, however, are situated on the right side of the heart and direct deoxygenated blood from the body to the lungs.

The peripheral venous system also includes a number of valves that prevent retrograde blood flow. By preventing retrograde blood flow, the valves found throughout the venous system assist the flow of blood through the veins and returning to the heart.

Normally, the mitral valve has two leaflets and the tricuspid valve has at least two, preferably three leaflets. The aortic and pulmonary valves, however, have normally at least two, preferably three leaflets, also often referred to as "cusps" because of their half-moon like appearance.

Venous valves are usually of the bicuspid type, with each cusp or leaflet forming a reservoir for blood, which, under pressure, forces the free edges of the cusps together to permit mostly antegrade blood flow to the heart. As discussed in detail below, since a majority of venous blood flow is against gravity while a person is standing, incompetent or destroyed venous valves can cause significant medical problems in the legs, ankles, and feet.

Valve diseases are typically classified into two major categories; stenosis and insufficiency. In the case of a stenosis, the native valve does not open properly, whereby insufficiency represents the opposite effect showing, deficient closing properties.

Insufficiency of the inlet (atrioventricular) tricuspid valve to the right ventricle of the heart results in regurgitation of blood back into the right atrium, which, serving to receive blood flow returning in the veins from the entire body, then results in turn in suffusion and swelling (edema) of all the organs, most notably in the abdomen and extremities, insufficient forward conduction of blood flow from the right ventricle into the lungs causing compromise of pulmonary function, and ultimately pump failure of the right heart. Collectively, these conditions are termed right heart failure; a condition that leads to incapacity and possibly to death if progressive and uncorrected.

Insufficiency of vein function due to the incompetence or destruction of peripheral venous valves leads to acute then chronic swelling of the veins and their dependent lymphatics and tissues. This condition can affect the deep veins of the body, commonly the lower extremities or pelvis, or the superficial veins of the lower extremities in particular, leading to progressive expansion of the veins and further valvular incompetence, a condition known as varicose veins.

Medical conditions like high blood pressure, inflammatory and infectious processes often lead to stenosis and insufficiency. Treatment of heart valve dysfunctions typically include reparation of the diseased heart valve with preservation of the patient's own valve or replacement of the valve with a mechanical or bioprosthetic valve (i.e. "tissue" valve), i.e. a prosthetic valve. Particularly for aortic heart valves, however, it is frequently necessary to introduce a heart valve replacement.

Various prosthetic heart valves have thus been developed for replacement of natural diseased or defective valves. Illustrative are the one-piece bioprosthetic "tissue" valves disclosed in Applicant's Co-Pending application Ser. No. 13/560,573.

A major drawback associated with most one-piece prosthetic valves is that the valves are typically sized and configured for replacement of a defined valve, i.e. aortic, pulmonary, mitral, tricuspid or peripheral venous valve. A sizable number of one-piece prosthetic valves must thus be produced to accommodate replacement of diseased or defective aortic, pulmonary, mitral, tricuspid or peripheral venous valves.

The implantation of a prosthetic valve, including mechanical valves and bioprosthetic valves, also requires a great deal of skill and concentration given the delicate nature of the native cardiovascular tissue and the spatial constraints of the surgical field. It is also critical to achieve a secure and reliable attachment of the valve to host cardiovascular tissue.

Various structures and means have thus been developed to provide a secure and reliable attachment of a prosthetic valve to host cardiovascular tissue. Most surgical techniques comprise suturing the ends of the valve to the annulus of the cardiovascular vessel.

There are numerous drawbacks and disadvantages associated with suturing a valve to host tissue. A major disadvantage is the high risk of perivalvular leakage.

In application Ser. No. 13/560,573, the tissue valve includes a sewing ring that can be employed to suture the ends of the valve to the annulus of the cardiovascular vessel. Although the use of a sewing ring to secure the valve to a cardiovascular vessel can be, and most times is, highly effective, success of the technique is still highly dependent on the skill of the surgeon.

There is thus a need to provide prosthetic valves that can be readily employed to selectively replace diseased or defective aortic, pulmonary, mitral, tricuspid and peripheral venous valves.

There is also a need to provide prosthetic valves having means for secure, reliable and consistent attachment to cardiovascular vessels.

It is therefore an object of the present invention to provide two-piece prosthetic tissue valves that can be readily employed to selectively replace diseased or defective aortic, pulmonary, mitral, tricuspid and peripheral venous valves.

It is another object of the present invention to provide two-piece prosthetic tissue valves having means for secure, reliable, and consistently highly effective attachment to cardiovascular vessels.

It is another object of the present invention to provide two-piece prosthetic tissue valves that substantially reduce or eliminate intimal hyperplasia after intervention in a vessel and the harsh biological responses associated with conventional polymeric and metal valves.

SUMMARY OF THE INVENTION

The present invention is directed to two-piece prosthetic valves having first and second members, a first end of the first member being sized and configured to receive a second end of the second member therein, the second end of the second member being secured to the first member at at least one commissure connection point to form at least one leaflet therein.

In some embodiments, the second end of the second member is secured to the first member at two commissure connection points to form two leaflets therein.

In some embodiments, the second end of the second member is secured to the first member at three commissure connection points to form three leaflets therein.

In a preferred embodiment of the invention, the first and second valve members comprise an extracellular matrix (ECM) material. According to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, omentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

In some embodiments of the invention, the first and/or second valve members (or material thereof) include at least one pharmacological agent, i.e. an agent that is capable of producing a desired biological effect in vivo, e.g., stimulation or suppression of cell division, stimulation or suppression of apoptosis, stimulation or suppression of an immune response, anti-bacterial activity, etc.

In some embodiments of the invention, the pharmacological agent comprises an anti-inflammatory agent.

In some embodiments of the invention, the pharmacological agent comprises a statin, i.e. a HMG-CoA reductase inhibitor.

In some embodiments of the invention, the two-piece prosthetic valves include at least one anchoring mechanism.

In some embodiments of the invention, the anchoring mechanism comprises at least one reinforcing ring or band that is positioned and secured at a desired position on or in the valve.

In some embodiments of the invention, the anchoring mechanism comprises at least two reinforcing rings that are positioned and secured at desired positions, e.g. proximal and distal ends, on or in the valve.

In a preferred embodiment of the invention, the anchoring mechanisms are designed and configured to position the two-piece valves proximate the wall of a vessel (i.e. host tissue thereof), and maintain contact therewith, for a predetermined temporary support time period.

In some embodiments of the invention, the support time period is within the process of tissue regeneration.

The two-piece prosthetic valves of the invention provide numerous advantages compared to prior art prosthetic valves. Among the advantages are the following:

The provision of two-piece prosthetic tissue valves that can be readily sized and configured to accommodate placement in various cardiovascular vessels, including aortic, pulmonary, mitral, tricuspid and/or peripheral venous vessels.

The provision of two-piece prosthetic tissue valves having multiple internal valves that can be readily sized and configured to accommodate placement in peripheral venous vessels.

The provision of two-piece prosthetic tissue valves having means for secure, reliable, and consistently highly effective attachment to cardiovascular vessels.

The provision of two-piece prosthetic tissue valves that include anchoring mechanisms that temporarily position the valves proximate cardiovascular tissue for a pre-determined period of time.

The provision of two-piece prosthetic tissue valves that exhibit optimum mechanical compatibility with vascular structures.

The provision of two-piece prosthetic tissue valves that substantially reduce or eliminate intimal hyperplasia after intervention in a vessel and the harsh biological responses associated with conventional polymeric and metal valves.

The provision of two-piece prosthetic tissue valves that induce host tissue proliferation, bioremodeling and regeneration of new tissue and tissue structures with site-specific structural and functional properties.

The provision of two-piece prosthetic tissue valves that are capable of administering a pharmacological agent to host tissue and, thereby produce a desired biological and/or therapeutic effect.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1:
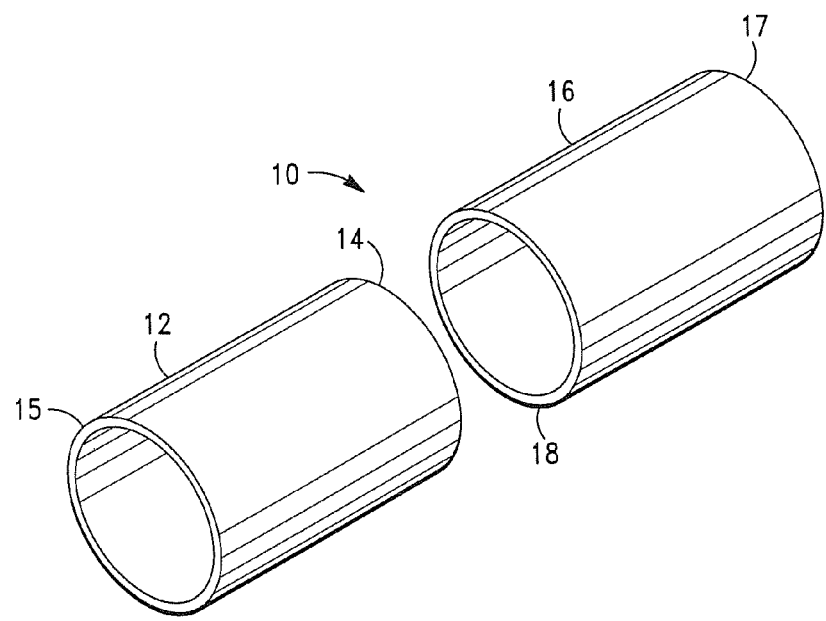
FIG. 1 is a perspective view of one embodiment of first and second pre-assembled valve members, in accordance with the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

DEFINITIONS

The terms "anchoring mechanism" and "anchor", as used herein in connection with some embodiments of the two-piece anchored valves, mean a temporary structure that is configured and employed to "temporarily" position the valve proximate vessel tissue. As discussed in detail herein, in some embodiments of the invention, the anchoring mechanisms are designed and configured to temporarily position tissue valves proximate a recipient's cardiovascular tissue for a predetermined period of time, which, in some embodiments, is preferably within the process of new tissue regeneration.

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, antiviral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

According to the invention, the terms "pharmacological agent", "active agent", "drug" and "active agent formulation" can further include, without limitation, the following growth factors: platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (1-IGF), insulin-like growth factor (IGF), nerve growth factor (NGF), platlet derived growth factor (PDGF), tumor necrosis factor alpha (TNA-alpha), and placental growth factor (PLGF).

The term is "pharmacological agent", "active agent", "drug" and "active agent formulation" further mean and include the following Class I-Class V antiarrhythmic agents: (Class Ia) quinidine, procainamide and disopyramide; (Class Ib) lidocaine, phenyloin and mexiletine; (Class Ic) flecamide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antiobiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent", "drug" and "active agent formulation" can further include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent", "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, propara-caine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocalne, ropivacaine, and trimecaine. Local anesthetics can further include combinations of the above from either amides or esters.

The terms "pharmacological agent", "active agent", "drug" and "active agent formulation" can further include one or more classes of cytotoxic anti-neoplastic agents or chemotherapy agents, including, without limitation, alkylating agents, cisplatin, carboplatin, oxaliplatin, mechlorethamine, cyclophosphamide, chlorambucil, and ifosfamide. Chemotherapy agents can also include, without limitation, antimetabolites, such as purine analogues, pyrimidine analogues and antifolates, plant alkaloids, such as vincristine, vinblastine, vinorelbine, vindesine, podophyllotoxin, etoposide and teniposide, taxanes, such as paclitaxel and docetaxel, topoisomerase inhibitors, such as irinotecan, topotecan, amsacrine, etoposide, etoposide phosphate and teniposide, cytotoxic antibiotics, such as actinomyocin, bleomycin, plicamycin, mytomycin and anthracyclines, such as doxorubicin, daunorubicin, valrubicin, idarubicin, epirubicin, and antibody treatments, such as abciximab, adamlimumab, alamtuzumab, basiliximab, belimumab, bevacizumab, brentuximab vedotin, canakinumab, cetuximab, certolizumab pego, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumumab, ranibizumab, rituximab, tocilizumab (atlizumab), tositumomab and trastuzumab.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofrofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The terms "cells" and "stem cells" are also used interchangeably herein, and mean and include an organism that has the potential to induce modulating proliferation, and/or growth and/or regeneration of tissue. Stem cells can thus include, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

According to the invention, the terms "pharmacological agent", "active agent", "drug" and "active agent formulation" can further include the following active agents (referred to interchangeably herein as a "protein", "peptide" and "polypeptide"): collagen (types I-V), proteoglycans, glycosaminoglycans (GAGs), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, ostepontins, and angiotensin converting enzymes (ACE).

The terms "active agent formulation", "pharmacological agent formulation" and "agent formulation", are also used interchangeably herein, and mean and include an active agent optionally in combination with one or more pharmaceutically acceptable carriers and/or additional inert ingredients. According to the invention, the formulations can be either in solution or in suspension in the carrier.

The term "pharmacological composition", as used herein, means and includes a composition comprising a "pharmacological agent" and/or a "pharmacological agent formulation" and/or any additional agent or component identified herein.

The term "therapeutically effective", as used herein, means that the amount of the "pharmacological composition" and/or "pharmacological agent" and/or "active agent formulation" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "delivery" and "administration" are used interchangeably herein, and mean and include providing a "pharmacological composition" or "pharmacological agent" or "active agent formulation" to biological tissue.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to two-piece prosthetic valves which, in some embodiments, are formed from extracellular matrix materials. According to the invention, the two-piece prosthetic valves of the invention can be readily designed and configured and, hence, employed to replace native valves in the body including, without limitation, diseased or defective aortic, pulmonary, mitral, tricuspid and/or peripheral venous valves.

As discussed in detail herein, the two-piece prosthetic valves include first and second members, a first end of the first member being sized and configured to receive a second end of the second member therein, the second end of the second member being secured to the first member at at least one commissure connection point to form at least one leaflet therein.

In some embodiments, the second end of the second member is secured to the first member at two commissure connection points to form two leaflets therein.

In some embodiments, the second end of the second member is secured to the first member at three commissure connection points to form three leaflets therein.

In some embodiments of the invention, the two-piece prosthetic valves also include an anchoring mechanism to position the valves proximate cardiovascular tissue, and maintain contact therewith for a pre-determined anchor support time period. Suitable anchoring mechanisms are disclosed in Applicant's Co-pending application Ser. No. 13/782,024, filed Mar. 1, 2013.

As will readily be appreciated by one having ordinary skill in the art, the two-piece valve structure can be readily sized and configured to accommodate placement in various cardiovascular vessels, including aortic, pulmonary, mitral, tricuspid and/or peripheral venous vessels.

The two-piece prosthetic valves of the invention can also be deployed in various cardiovascular vessels by traditional or minimally invasive means.

According to the invention, the first and second valve members and, hence, two-piece valves formed therefrom, can comprise various biocompatible materials, including, without limitation, Dacron and mammalian tissue, e.g., bovine tissue.

In some embodiments of the invention, the first and second valve members comprise an extracellular matrix (ECM) material (two-piece valves formed therefrom hereinafter referred to as "two-piece tissue valves").

According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety. The mammalian tissue sources include, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

According to the invention, ECM material can comprise, in whole or in part, just the basement membrane (or transitional epithelial layer) with the subadjacent tunica propria, the tunica submucosa, tunica muscularis, and tunica serosa. The extracellular matrix component of the ECM material can thus contain any or all of these layers or only the basement membrane portion, excluding the submucosa.

As stated above, in some embodiments of the invention, the first and/or second valve members and, hence, two-piece tissue valves formed therefrom include at least one pharmacological agent or composition, i.e. an agent that is capable of producing a desired biological effect in vivo, such as stimulation or suppression of cell division, stimulation or suppression of apoptosis, stimulation or suppression of an immune response, anti-bacterial activity, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises an anti-inflammatory agent. According to the invention, suitable anti-inflammatory agents include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, morniflumate, nabumetone, nandrolone, naproxen, naproxen sodium, naproxol, nimazone, olsalazine sodium, orgotein, orpanoxin, oxandrolone, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

In some embodiments of the invention, the pharmacological agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that the noted statins exhibit numerous beneficial properties that provide several beneficial biochemical actions or activities. The properties and beneficial actions are set forth in Applicant's Co-Pending application Ser. No. 13/373,569, filed on Sep. 24, 2012 and Ser. No. 13/782,024, filed on Mar. 1, 2013; which are incorporated by reference herein in their entirety.

According to the invention, the two-piece prosthetic valves can include 10 mg or greater of a statin to achieve a higher concentration of the statin within a desired tissue, or 10 ug or less to achieve a lower concentration of the statin within a desired tissue.

In some embodiments of the invention, the two-piece prosthetic valves also include chitosan or a derivative thereof. As also set forth in detail in Co-Pending application Ser. No. 13/573,569, chitosan also exhibits numerous beneficial properties that provide several beneficial biochemical actions or activities.

In some embodiments of the invention, the two-piece prosthetic valves (or material thereof) include a cell. According to the invention, the cell can comprise, without limitation, a stem cell, such as, for example, a human embryonic stem cell, fetal cell, fetal cardiomyocyte, myofibroblast, mesenchymal stem cell, autotransplanted expanded cardiomyocyte, adipocyte, totipotent cell, pluripotent cell, blood stem cell, myoblast, adult stem cell, bone marrow cell, mesenchymal cell, embryonic stem cell, parenchymal cell, epithelial cell, endothelial cell, mesothelial cell, fibroblast, myofibroblast, osteoblast, chondrocyte, exogenous cell, endogenous cell, stem cell, hematopoetic stem cell, pluripotent stem cell, bone marrow-derived progenitor cell, progenitor cell, myocardial cell, skeletal cell, undifferentiated cell, multi-potent progenitor cell, unipotent progenitor cell, monocyte, cardiomyocyte, cardiac myoblast, skeletal myoblast, macrophage, capillary endothelial cell, xenogenic cell, and allogenic cell.

In some embodiments of the invention, the two-piece prosthetic valves (or material thereof) include a protein. According to the invention, the protein can comprise, without limitation, a growth factor, collagen, proteoglycan, glycosaminoglycan (GAG) chain, glycoprotein, cytokine, cell-surface associated protein, cell adhesion molecule (CAM), angiogenic growth factor, endothelial ligand, matrikine, matrix metalloprotease, cadherin, immunoglobin, fibril collagen, non-fibrillar collagen, basement membrane collagen, multiplexin, small-leucine rich proteoglycan, decorin, biglycan, fibromodulin, keratocan, lumican, epiphycan, heparan sulfate proteoglycan, perlecan, agrin, testican, syndecan, glypican, serglycin, selectin, lectican, aggrecan, versican, nuerocan, brevican, cytoplasmic domain-44 (CD44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-beta), fibroblast growth factor-2 (FGF-2) (also called basic fibroblast growth factor (bFGF)), thrombospondin, osteopontin, angiotensin converting enzyme (ACE), and vascular epithelial growth factor (VEGF).

As indicated above, in some embodiments of the invention, the two-piece prosthetic valves of the invention, including two-piece tissue valves, further include at least one anchoring mechanism. According to the invention, the anchoring mechanisms can comprise various forms and materials.

In some embodiments of the invention, the anchoring mechanisms comprise reinforcing rings or bands that are positioned and secured at desired positions, e.g. proximal and distal ends, on or in a two-piece valve. According to the invention, the reinforcing rings and bands preferably comprise a biocompatible material, such as a biocompatible metal, e.g., Nitinol® and stainless steel, and various polymeric materials. The reinforcing rings and bands can also comprise various biodegradable materials, such as magnesium and ECM material.

As defined above and discussed in detail in Co-pending application Ser. No. 13/782,024, the terms "anchoring mechanism" and "anchor", as used in connection with some embodiments of anchored two-piece valves of the invention, including anchored two-piece tissue valves, mean a structure that is configured and employed to temporarily position a two-piece valve of the invention proximate host tissue of a vessel. The function of such an anchoring mechanism is thus to temporarily support and position a two-piece valve of the invention proximate host tissue of a cardiovascular vessel, i.e. vessel wall.

In some embodiments, the anchoring mechanisms position the anchored two-piece "tissue" valves proximate host tissue of a vessel, and maintain contact therewith for a predetermined temporary anchor support period of time within the process of tissue regeneration.

Referring now to FIGS. 1-6, one embodiment of a two-piece prosthetic tissue valve and method for forming same will be described in detail. As illustrated in FIG. 1, the two-piece prosthetic valve 10 includes first 12 and second 16 members. In a preferred embodiment, the first and second members 12, 16 preferable comprise substantially tubular members.

In a preferred embodiment, the first 12 and second 16 members comprise an extracellular matrix (ECM) material. According to the invention, the ECM material can be derived from various mammalian tissue sources including, without limitation, small intestinal submucosa, stomach submucosa, large intestinal tissue, urinary bladder submucosa, liver basement membrane, pericardium, epicardium, endocardium, myocardium, lung tissue, kidney tissue, pancreatic tissue, prostate tissue, mesothelial tissue, fetal tissue, a placenta, a ureter, veins, arteries, heart valves with or without their attached vessels, tissue surrounding the roots of developing teeth, and tissue surrounding growing bone.

In some embodiments of the invention, the first 12 and/or second 16 members and, hence, ECM based two-piece tissue valves formed therefrom, include at least one pharmacological agent or composition. Suitable pharmacological agents and compositions include, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises a statin, i.e. a HMG-CoA reductase inhibitor. Suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

In some embodiments of the invention, the pharmacological agent comprises an anti-inflammatory agent.

In a preferred embodiment, a first end 14 of the first member 12 is sized and configured to receive a second end 18 of the second member 16 therein. Thus, in some embodiments of the invention, the outer diameter of the second member 16 is slightly smaller than the inner diameter of the first member 12.

According to the invention, the first 12 and second 16 members can comprise various desired lengths, whereby additional member material can be provided at the second end 15 of the first member 12 and/or first end 17 of the second member 16 to allow a surgeon to control the placement of a two-piece valve on a target vessel, e.g., aorta.

As discussed below, the length of the second member end 18 that is disposed within the first member 12, i.e. $C_h$, determines the height of the commissures or leaflets (or cusps) relative to the annulus.

Figure 2:
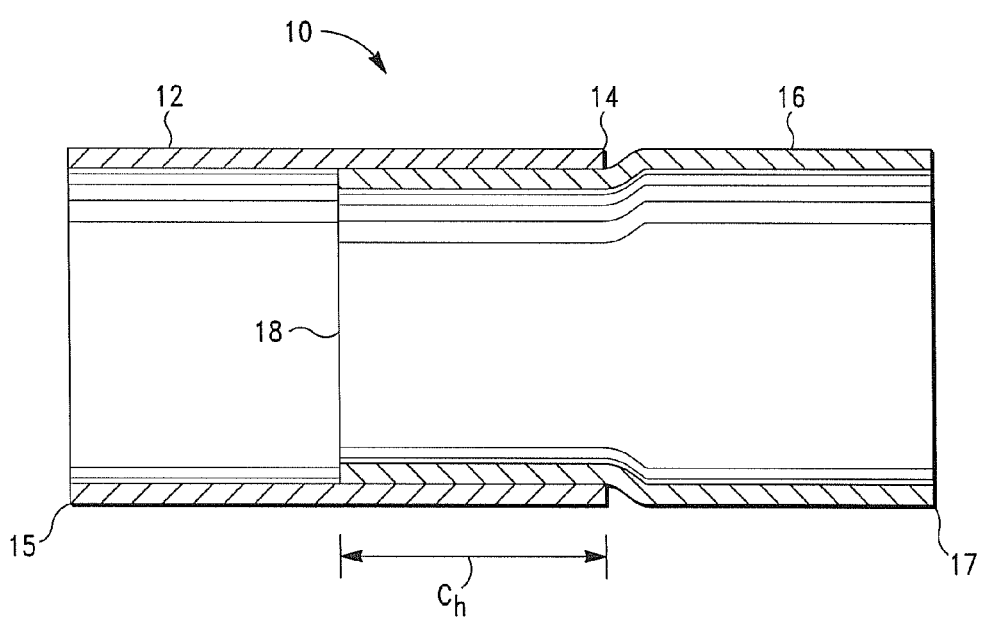
FIG. 2 is a side plan, sectional view of an assembled two-piece prosthetic valve, in accordance with the invention.

Referring now to FIG. 2, after the second end 18 of the second member 16 is disposed in the first end 14 of the first member 12, the second member end 18 is secured, i.e. sutured, to the first member 12 at at least one commissure connection point (denoted "20a" in FIG. 5) to form at least one leaflet therein that is configured to selectively prevent undesired regurgitation of blood through the valve structure (denoted "30a").

In some embodiments, the second member end 18 is secured to the first member 12 at two commissure connection points (denoted "20b" and "20c" in FIG. 6) to form two leaflets therein (denoted "30b" and "30c").

In some embodiments, the second member end 18 is secured to the first member 12 at three, preferably, equally spaced positions (denoted "20d", "20e" and "20f" in FIG. 4) to commissure connection points to form three leaflets therein (denoted "30d", "30e" and "30f").

According to the invention, the commissure connection points 20a-20f can be achieved (or provided) by spot sutures at the connection points. One or more of the commissure connection points 20a-20f, or one or more additional commissure connection points can also be achieved via one or more longitudinal sutures (denoted "22") along the length of the second member end 18 that is disposed within the first member 12.

Figure 3:
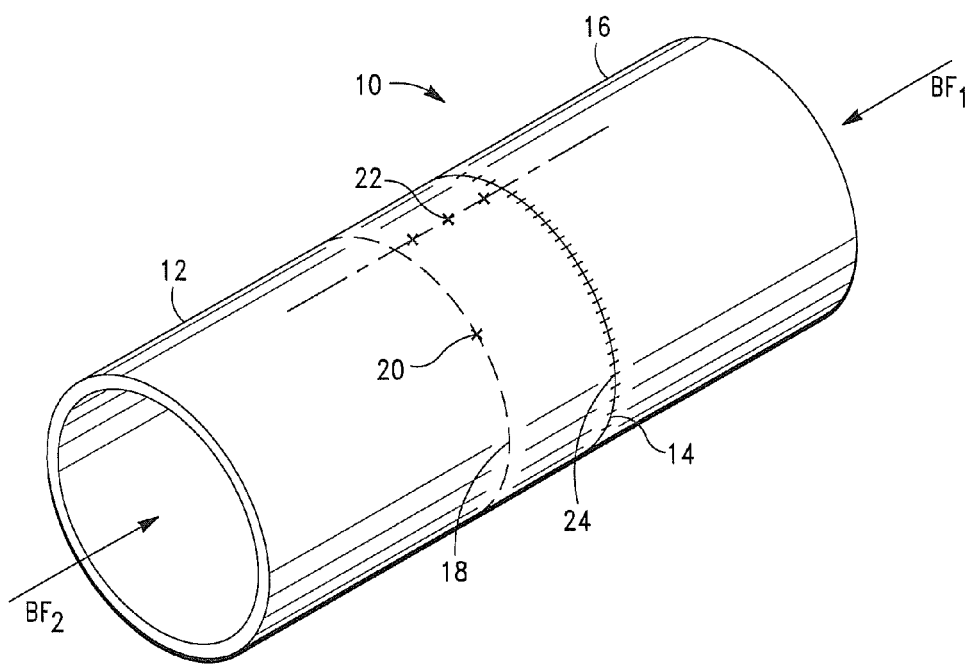
FIG. 3 is a perspective view of the two-piece prosthetic valve shown in FIG. 2, showing one embodiment of commissure connection points, in accordance with the invention.

As also illustrated in FIG. 3, the first member end 14 is also preferably sutured 24 to the second member 16 proximate the second end 18 thereof to provide a sealed connection of the first and second members 12, 16.

Figure 4:
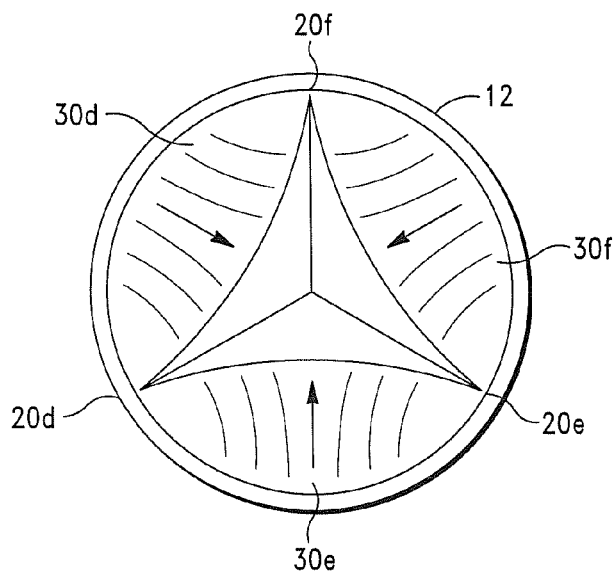
FIG. 4 is a front (or end) plan view of one embodiment of a two-piece prosthetic valve having three leaflets formed therein, in accordance with the invention.
Figure 5:
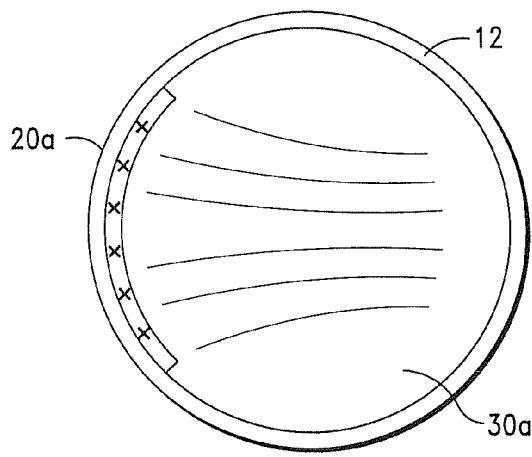
FIG. 5 is a front plan view of another embodiment of a two-piece prosthetic valve having one leaflet formed therein, in accordance with the invention.
Figure 6:
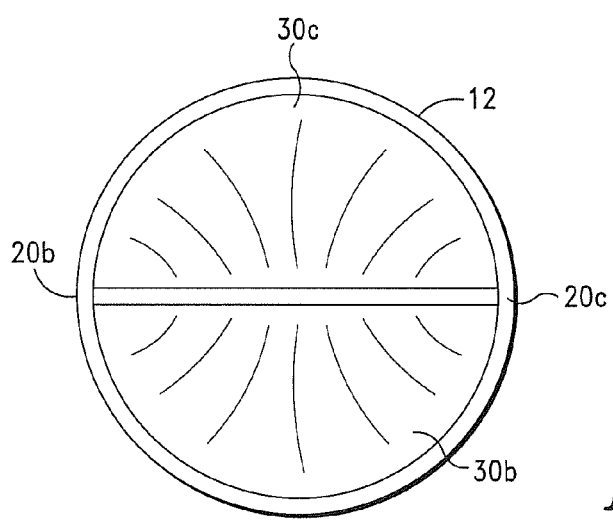
FIG. 6 is a front plan view of another embodiment of a two-piece prosthetic valve having two leaflets formed therein, in accordance with the invention.

According to the invention, when a two-piece valve of the invention is deployed in a cardiovascular vessel, the valve allows normal blood flow therethrough in the direction denoted by Arrow "BF₁" and selectively restricts regurgitation of blood in the direction denoted by Arrow BF₂, i.e. the leaflets formed by suturing the second member end 18 to the first member 12 expand and restrict fluid flow therethrough (see FIG. 4).

If the two-piece valve comprises an ECM based two-piece tissue valve, the ECM based two-piece tissue valve will also induce host tissue proliferation, bioremodeling, including neovascularization, e.g., vasculogenesis, angiogenesis, and intussusception, and regeneration of tissue structures with site-specific structural and functional properties.

According to the invention, the leaflets 30a-30f can have various shapes and sizes, such as shown in U.S. Pat. No. 8,257,434 and Co-pending application Ser. No. 13/560,573, which are incorporated by reference herein.

As indicated above, the shape and length of each leaflet 30a-30f, i.e. valve structure, is, of course, dependent upon the commissure connection points of the second member end 18 and the size, i.e. operative diameter, of the first member 12 member and, hence, valve formed therefrom.

In some embodiments, the edge length of each leaflet 30a-30f ranges from approximately 10 mm to approximately 70 mm, more preferably from approximately 15 mm to approximately 60 mm, and most preferably from approximately 25 mm to approximately 45 mm. In this aspect, it is contemplated that the ratio between the edge length of each leaflet to the diameter of a target annulus can range from approximately 0.5:1 to approximately 3:1, and more preferably from approximately 1:1 to approximately 2:1. In addition to the noted ratios serving as the endpoints of the ranges set forth above, the disclosed ranges also include all ratios falling between the endpoint ratios.

The size or operative diameter and length of the two-piece valves of the invention, including valve 10, described above, can also vary to accommodate placement in various adult and pediatric cardiovascular vessels.

In some embodiments of the invention, the two-piece prosthetic valve 10 further includes at least one anchoring mechanism. In some embodiments, the anchoring mechanisms comprise reinforcing rings or bands that are positioned and secured at desired positions, e.g. proximal and distal ends, on or in a two-piece valve.

According to the invention, the anchoring mechanisms are designed and configured to position the two-piece valves proximate host tissue of a vessel, and maintain contact therewith for a predetermined anchor support period of time.

As will readily be appreciated by one having ordinary skill in the art, a tubular structure having multiple valves can also be provided by the valve forming method of the invention. Such a structure, i.e. prosthetic multi-valve vessel, is particularly applicable for replacement of defective peripheral venous valves.

A single prosthetic multi-valve vessel would also facilitate a simplified delivery and, in some instances, a percutaneous delivery.

In one envisioned embodiment of the prosthetic multi-valve vessel, the prosthetic valves have a pre-determined spacing, preferably, a spacing matching the spacing of the natural venous valves.

A prosthetic multi-valve vessel having two prosthetic valves can thus be implanted in a peripheral venous vessel possessing chronic venous insufficiency (CVI), i.e. two valves lacking coaptation, to address the CVI.

As will readily be appreciated by one having ordinary skill in the art, the two-piece valves of the invention can thus be readily sized and configured to accommodate placement in various cardiovascular vessels, including aortic, pulmonary, mitral, tricuspid and/or peripheral venous vessels.

As will readily be appreciated by one having ordinary skill in the art, the present invention provides numerous advantages compared to prior art prosthetic valves. Among the advantages are the following:

The provision of two-piece prosthetic tissue valves that can be readily sized and configured to accommodate placement in various cardiovascular vessels, including aortic, pulmonary, mitral, tricuspid and/or peripheral venous vessels.

The provision of two-piece prosthetic tissue valves having multiple internal valves that can be readily sized and configured to accommodate placement in peripheral venous vessels.

The provision of two-piece prosthetic tissue valves having means for secure, reliable, and consistently highly effective attachment to cardiovascular vessels.

The provision of two-piece prosthetic tissue valves that include anchoring mechanisms that temporarily position the valves proximate cardiovascular tissue for a pre-determined period of time.

The provision of two-piece prosthetic tissue valves that exhibit optimum mechanical compatibility with vascular structures.

The provision of two-piece prosthetic tissue valves that substantially reduce or eliminate intimal hyperplasia after intervention in a vessel and the harsh biological responses associated with conventional polymeric and metal valves.

The provision of two-piece prosthetic tissue valves that induce host tissue proliferation, bioremodeling and regeneration of new tissue and tissue structures with site-specific structural and functional properties.

The provision of two-piece prosthetic tissue valves that are capable of administering a pharmacological agent to host tissue and, thereby produce a desired biological and/or therapeutic effect.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A two-piece prosthetic valve assembly, consisting of:
a bioremodelable first conduit member having first and second ends, and an internal lumen, said first conduit member lumen having an inner surface; and
a separate bioremodelable second conduit member having first and second ends, and an internal lumen,
said first and second conduit members comprising an extracellular matrix (ECM) material from a mammalian tissue source, said tissue source comprising small intestine submucosa (SIS),
said first end of said first conduit member being configured to receive said second end of said second conduit member therein, wherein said second end of said second conduit member is disposed in said first end of said first conduit member, said second end of said second conduit member being directly attached to said first conduit member lumen inner surface at a first commissure connection point, wherein said first conduit member lumen and said second conduit member lumen are in communication, and wherein a first valve leaflet is formed by said second end of said second conduit member within said first conduit member lumen, said first valve leaflet being configured to selectively restrict fluid flow through said two-piece valve assembly, and
wherein, following attachment of said valve assembly to a cardiovascular vessel, said first and second conduit members are remodeled by cardiovascular tissue to form an integral valve member comprising remodeled cardiovascular tissue.

2. The two-piece valve assembly of claim 1, wherein said second end of said second conduit member is attached to said first conduit member lumen inner surface at two commissure connection points, and wherein first and second valve leaflets are formed within said first conduit member lumen.

3. The two-piece valve assembly of claim 1, wherein said second end of said second conduit member is attached to said first conduit member lumen inner surface at three commissure connection points, and wherein first, second and third valve leaflets are formed within said first conduit member lumen.

4. The two-piece valve assembly of claim 1, wherein said attached first and second conduit members have substantially coincident longitudinal axes.

5. The two-piece valve assembly of claim 4, wherein said three commissure connection points are positioned substantially within a common plane, said common plane being substantially perpendicular to said substantially coincident longitudinal axes of said first and second conduit members.

6. The two-piece valve assembly of claim 1, wherein said first end of said first member is sealably attached to said second end of said second member.

7. The two-piece valve assembly of claim 1, wherein said tissue source is selected from the group consisting of urinary bladder submucosa (UBS), stomach submucosa (SS), central nervous system tissue, epithelium of mesodermal origin, dermal extracellular matrix, subcutaneous extracellular matrix, gastrointestinal extracellular matrix, tissue surrounding growing bone, placental extracellular matrix, ornamentum extracellular matrix, cardiac extracellular matrix, kidney extracellular matrix, pancreas extracellular matrix, lung extracellular matrix, and combinations thereof.

8. The two-piece valve assembly of claim 1, wherein said ECM material further includes an additional pharmacological agent.

9. The two-piece valve assembly of claim 8, wherein said pharmacological agent comprises an anti-inflammatory.

10. The two-piece valve assembly of claim 8, wherein said pharmacological agent comprises a statin.

11. The two-piece valve assembly of claim 10, wherein said statin is selected from the group consisting of atorvastatin, cerivastatin, fluvastatin, lovastatin, mevastatin, pitavastatin, pravastatin, rosuvastatin and simvastatin.

12. The two-piece valve assembly of claim 8, wherein said pharmacological agent comprises a growth factor.

13. The two-piece valve assembly of claim 12, wherein said growth factor is selected from the group consisting of a platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-alpha), and placental growth factor (PLGF).

14. The two-piece valve assembly of claim 8, wherein said pharmacological agent comprises an anti-arrhythmic agent.

15. The two-piece valve assembly of claim 14, wherein said anti-arrhythmic agent is selected from the group comprising quinidine, procainamide, disopyramide, lidocaine, phenyloin, mexiletine, flecamide, propafenone, moricizine, propranolol, esmolol, timolol, metoprolol, atenolol, amiodarone, sotalol, ibutilide, dofetilide, verapamil, diltiazem, adenosine and digoxin.

16. A two-piece prosthetic valve assembly, consisting of:
a bioremodelable first conduit member having first and second ends, and an internal lumen, said first conduit member lumen having an inner surface; and a separate bioremodelable second conduit member having first and second ends, and an internal lumen, said first and second conduit members comprising an extracellular matrix (ECM) material from a mammalian tissue source, said tissue source comprising small intestine submucosa (SIS), said SIS further comprising an exogenously added pharmacological agent, said pharmacological agent comprising a statin selected from the group consisting of atorvastatin, cerivastatin, fluvastatin, lovastatin, mevastatin, pitavastatin, pravastatin, rosuvastatin and simvastatin, said first end of said first conduit member being configured to receive said second end of said second conduit member therein, wherein said second end of said second conduit member is disposed in said first end of said first conduit member, said second end of said second conduit member being directly attached to said first conduit member lumen inner surface at a first commissure connection point, wherein said first conduit member lumen and said second conduit member lumen are in communication, and wherein a first valve leaflet is formed by said second end of said second conduit member within said first conduit member lumen, said first valve leaflet being configured to selectively restrict fluid flow through said two-piece valve assembly, and wherein, following attachment of said valve assembly to a cardiovascular vessel, said first and second conduit members are remodeled by cardiovascular tissue to form an integral valve member comprising remodeled cardiovascular tissue.

17. The two-piece valve assembly of claim 16, wherein said second end of said second conduit member is attached to said first conduit member lumen inner surface at two commissure connection points, and wherein first and second valve leaflets are formed within said first conduit member lumen.

18. The two-piece valve assembly of claim 16, wherein said second end of said second conduit member is attached to said first conduit member lumen inner surface at three commissure connection points, and wherein first, second and third valve leaflets are formed within said first conduit member lumen.

19. The two-piece valve assembly of claim 16, wherein said pharmacological agent comprises an anti-arrhythmic agent selected from the group comprising quinidine, procainamide, disopyramide, lidocaine, phenyloin, mexiletine, flecamide, propafenone, moricizine, propranolol, esmolol, timolol, metoprolol, atenolol, amiodarone, sotalol, ibutilide, dofetilide, verapamil, diltiazem, adenosine and digoxin.

* * * * *